United States Patent [19]

Wright

[11] Patent Number: 4,593,099

[45] Date of Patent: Jun. 3, 1986

[54] (TETRAZOLYL) THIENOPYRIDINONES

[75] Inventor: Terry L. Wright, Antioch, Calif.

[73] Assignee: Merrell Dow Pharmaceuticals Inc., Cincinnati, Ohio

[21] Appl. No.: 659,397

[22] Filed: Oct. 10, 1984

[51] Int. Cl.$^4$ .................................... C07D 495/04
[52] U.S. Cl. .................................................. 546/114
[58] Field of Search ........................................ 546/114

[56] References Cited

U.S. PATENT DOCUMENTS 2,977,372  3/1961  Finnegan et al. ................... 548/250

Primary Examiner—Henry R. Jiles
Assistant Examiner—Bernard I. Dentz
Attorney, Agent, or Firm—John J. Kolano

[57] ABSTRACT (1H-Tetrazol-5-yl)thienopyridinones and related compounds which are useful as antiallergic agents are described herein. The compounds are prepared by the reaction of an appropriate cyanoketone with ammonium chloride and an azide such as sodium azide in an inert solvent such as dimethylformamide.

3 Claims, No Drawings

(TETRAZOLYL) THIENOPYRIDINONES

The present invention relates to compounds having a thienopyridine fused ring system with a tetrazole substituent. These compounds can be represented by the following general formula:

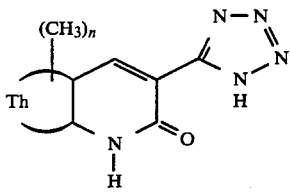

wherein Th is a thiophene fused to the pyridine ring and n is 0, 1 or 2; and the pharmaceutically acceptable salts thereof. Three isomers are possible depending on the manner of fusion of the thiophene ring and all three isomers are encompassed by the present invention. In one of the isomers, the ring system is thieno[3,2-b]pyridinone and it has the following specific structural formula:

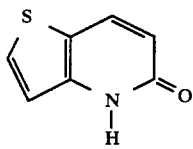

The compounds containing this specific ring system are a preferred embodiment of this invention.

Equivalent to the above tetrazoles for the purposes of this invention are the pharmaceutically acceptable salts and also the hydrates of the compounds and their salts. The term "pharmaceutically acceptable salt" as used herein is intended to include non-toxic cationic salts such as the alkali metal salts, e.g., sodium and potassium; alkaline earth metal salts such as calcium, magnesium or barium; salts with ammonia; and salts with organic bases, e.g., amines such as triethylamine, n-propylamine, tri-n-butylamine, trimethamine, triethanolamine and N-methylglucamine. While the indicated salts can be considered as equivalent to the tetrazoles as far as pharmacological effects are concerned, certain of these salts have the further advantage of better physical properties. Thus, for example, they give solid form which can be handled much more easily than the tetrazole itself.

The compounds of the present invention are prepared from a cyanoketone of the formula:

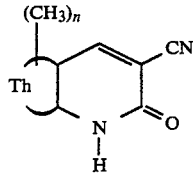

wherein Th and n are defined as above. The cyanoketone is heated with ammonium chloride and sodium azide in an inert solvent such as dimethylformamide. Sodium azide is the preferred azide although other alkali metal azides could also be used.

The starting material referred to above can be prepared by starting with an appropriate acetamido-substituted thiophene. This is heated with dimethylformamide and phosphorus oxychloride and, after the initial reaction is complete, hydroxylamine (hydrochloride) is added to the reaction mixture. In the process, cyclization to form a pyridine ring takes place and a chloro cyano substituted product having the following formula is obtained:

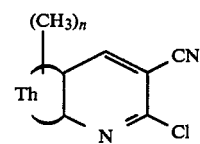

Alternatively, the chloro cyano compound can be prepared from an oxime of the formula:

wherein n is defined as above. The oxime is obtained from the corresponding ketone and hydroxylamine (hydrochloride) by standard procedures. The indicated oxime is treated with phosphoryl chloride in a Beckmann rearrangement to give the corresponding acetamide compound and this is reacted further as described above for the acetamido compound. In carrying out this process, it is not necessary to isolate the acetamide compound.

The chloro cyano compound is then converted to the corresponding iodide using sodium iodide and concentrated hydrochloric acid in acetonitrile and the iodo compound is then hydrolyzed to the desired ketone using acetic acid.

The tetrazoles of the present invention are converted to the corresponding pharmaceutically acceptable salts by reacting them with a substantially equimolar amount of the appropriate base in an aqueous solution or in a suitable organic solvent such as methanol or ethanol. The salts are recovered by standard methods such as filtration if they are insoluble in the original medium, or, if they are soluble in that medium, the salt is precipitated by evaporation of the solvent or by addition of a non-solvent for the salt.

The compounds of the present invention possess antiallergic activity. Thus, they are useful in the treatment of conditions in which antigen-antibody reactions are responsible for disease and particularly in the treatment of allergic diseases such as (but not limited to) extrinsic asthma, hay fever, urticaria, eczema or atopic dermatitis and upper respiratory conditions such as allergic rhinitis.

The compounds of the present invention may be administered either as individual therapeutic agents or as mixtures with other therapeutic agents. They may be administered alone but are generally administered in the form of pharmaceutical compositions, i.e., mixtures of the active agents with suitable pharmaceutical carriers or diluents. Examples of such compositions include tablets, lozenges, capsules, powders, aerosol sprays, aqueous or oily suspensions, syrups, elixirs and aqueous solutions for injection.

The nature of the pharmaceutical composition and the pharmaceutical carrier or diluent will, of course, depend on the desired route of administration, i.e., orally, parenterally or by inhalation. Oral compositions may be in the form of tablets or capsules and may contain conventional excipients such as binding agents (e.g., syrup, acacia, gelatin, sorbitol, tragacanth or polyvinylpyrrolidone), fillers (e.g., lactose, sugar, maizestarch, calcium phosphate, sorbitol or glycine), lubricants (e.g., magnesium stearate, talc, polyethylene glycol or silica), disintegrants (e.g., starch) or wetting agents (e.g., sodium lauryl sulfate). Oral liquid preparations may be in the form of aqueous or oily suspensions, solutions, emulsions, syrups, elixirs, etc., or may be presented as a dry product for reconstitution with water or other suitable vehicle before use. Such liquid preparations may contain conventional additives such as suspending agents, flavoring agents, diluents or emulsifying agents. For parenteral administration or inhalation, solutions or suspensions of a compound of the present invention with conventional pharmaceutical vehicles may be employed, e.g., as an aerosol spray for inhalation, as an aqueous solution for intravenous injection or as an oily suspension for intramuscular injection. The compounds may also be administered by means of inhalers or other devices which permit the active compounds in the form of dry powders to come into direct contact with the lungs. Procedures for the preparation of compositions as discussed above are described in standard texts, such as *Remington's Pharmaceutical Sciences*, Mack Publishing Company, Easton, Pa.

The compounds of the present invention or pharmaceutical compositions thereof may be administered to human asthmatic patients in single oral doses of approximately 1–1000 mg of active ingredient and multiple oral doses totaling up to about 4000 mg/day of active ingredient. When administered by inhalation, lower doses are generally given, i.e., on the order of about 0.1 of the normal dosage for the particular compound in question. These values are illustrative only, however, and the physician of course will ultimately determine the dosage most suitable for a particular patient on the basis of factors such as age, weight, diagnosis, severity of the symptoms and the particular agent to be administered.

The antiallergic activity of the present compounds is demonstrated by the IgE mediated rat Passive Cutaneous Anaphylaxis (PCA) test. This test is generally accepted at one of the best animal models for the qualitative determination of antiallergic activity. Disodium cromoglycate is active in this test when administered i.p. but not orally. The method can be described briefly as follows:

PCA Test Method

1. Antisera—Various standard methods described in the literature were used for the preparation of reaginic antisera to ovalbumin in either Hooded Lister or Brown Norway adult rats.
2. Animals—Adult male Sprague-Dawley or female Wistar Kyoto rats were used as antisera recipients in the test. The animals were allowed to acclimate for 5–14 days with food and water ad lib.
3. Sensitization—Recipient rats were passively sensitized by the intradermal injection of 100 microliters of two dilutions of antiserum (one injection on each side of the back). Sensitization occurred 48–72 hours prior to antigen challenge.
4. Administration of Test Compound—Four to six animals were used for each test compound/dilution. Compounds were homogenized in an appropriate carrier solution, and administered i.p. at 60 mg/kg 5 minutes prior to challenge.
5. Antigen Challenge and Reaction Evaluation—Ovalbumin (0.1–1.0 mg in a 0.5% solution of Evan's Blue Dye) in saline were given to each rat by i.v. administration. Thirty minutes later, the resultant PCA reactions were measured for average diameter and color intensity from the reflected surface of the skin. Test compound activity is expressed as percent inhibition based on control reactions.

When tested by the above procedure, the compounds of the present invention were active i.p.

The following examples are presented to illustrate the present invention but they should not be construed as limiting in any way.

EXAMPLE 1

To a mixture of 23 g of phosphoryl chloride and 4.3 g of dimethylformamide at room temperature was added 3.0 g of N-(3-thienyl)acetamide. The resulting solution was heated to reflux for 1.5 hours and then 2 g of hydroxylamine hydrochloride was added slowly over a period of 10 minutes. After the reaction subsided, the mixture was cooled to 25° C. and filtered. The solid collected in this way was washed with water and dried to give 5-chlorothieno[3,2-b]pyridine-6-carbonitrile as a light yellow solid melting at about 222°–224° C.

EXAMPLE 2

A solution was prepared from 5.0 g of 3-acetylthiophene oxime (obtained from the reaction of 3-acetylthiophene and hydroxylamine hydrochloride by standard procedures) and 100 ml of ether and cooled to 10° C. with an ice bath. Phosphoryl chloride (32 ml) was then added dropwise over a period of 20 minutes. A white precipitate formed during this addition and the resulting heterogeneous mixture was stirred at 10°–20° C. for 2 hours. Dimethylformamide (6.5 g) was then added dropwise and the mixture was heated to boil off the ether. Heating was continued until all the ether had been removed and the temperature of the reaction mixture reached 110° C. Heating at 110° C. was continued for 1 hour and then 4.9 g of hydroxylamine hydrochloride was added in portions over 15 minutes. The mixture was maintained at 110° C. for an additional 15 minutes and then allowed to cool to room temperature. The resulting mixture was poured into a mixture of 200 g of ice and 300 g of water with stirring. The heavy yellow precipitate which formed was collected by filtration and dried to give 5-chlorothieno[3,2-b]pyridine-6-carbonitrile.

EXAMPLE 3

A suspension was prepared from 25 g of 5-methyl-2-acetylthiophene oxime (obtained by reacting the appropriate ketone with hydroxylamine hydrochloride by standard procedures) and 250 ml of ether and this was cooled to 10° C. in an ice bath. Phosphoryl chloride (80 ml) was then added to the stirred suspension over a period of 15 minutes. The mixture was then allowed to warm to room temperature over a period of 16 hours. Then, 21 g of dimethylformamide was added over 10 minutes and the mixture was heated to 110° C. to boil off the ether. Heating was continued at 110° C. for 3.5 hours and then 11.2 g of hydroxylamine hydrochloride was added in portions over 20 minutes. The mixture was cooled and poured into 700 ml of water and the precipitate which formed was collected by filtration. This was recrystallized from acetone to give 2-methyl-6-chlorothieno[2,3-b]pyridine-5-carbonitrile melting at about 171°–173° C.

EXAMPLE 4

4-Chloro-2,7-dimethylthieno[3,4-b]pyridine-5-carboxaldehyde is reacted with hydroxylamine hydrochloride and phosphoryl chloride by standard procedures to give 4-chloro-2,7-dimethylthieno[3,4-b]pyridine-5-carbonitrile.

EXAMPLE 5

A solution of 5 g of 5-chlorothieno[3,2-b]pyridine-6-carbonitrile, 10 g of sodium iodide and 1 ml of concentrated hydrochloric acid in 70 ml of acetonitrile was heated at reflux for 65 hours. The mixture was then poured into water and the resulting solid was separated by filtration. The solid was recrystallized from acetone to give 5-iodothieno[3,2-b]pyridine-6-carbonitrile as white needles melting at about 190°–191° C.

If the above procedure is repeated using the products obtained in Examples 3 and 4, the products obtained are, respectively, 2-methyl-6-iodothieno[2,3-b]pyridine-5-carbonitrile and 4-iodo-2,7-dimethylthieno[3,4-b]pyridine-5-carbonitrile.

EXAMPLE 6

A mixture of 4.5 g of 5-iodothieno[3,2-b]pyridine-6-carbonitrile, 2.8 g of sodium acetate and 50 ml of acetic acid was heated at reflux for 48 hours. The mixture was then cooled and poured into water and the resulting solid was collected by filtration and recrystallized from dimethylformamide. This gave 5(4H)-oxothieno[3,2-b]pyridine-6-carbonitrile as a gray crystalline powder melting at greater than 300° C.

If the above procedure is repeated using the iodo compounds obtained in the second paragraph of Example 5, the products obtained are, respectively, 2-methyl-6(7H)-oxothieno[2,3-b]pyridine-5-carbonitrile and 2,7-dimethyl-4(3H)-oxothieno[3,4-b]pyridine-5-carbonitrile.

EXAMPLE 7

A mixture of 4 g of 5(4H)-oxothieno[3,2-b]pyridine-6-carbonitrile, 1.5 g of ammonium chloride and 1.8 g of sodium azide in 80 ml of dimethylformamide was heated at 110° C. with stirring for 18 hours. The reaction mixture was cooled, poured into 400 ml of water and acidified to a pH of 2 with concentrated hydrochloric acid. The solid which formed was separated by filtration and dried to give a gray powder. This crude product was purified by dissolving it in 100 ml of hot 10% aqueous sodium hydroxide solution, treating the solution with charcoal and filtering and then acidifying the filtrate with concentrated hydrochloric acid. The solid which formed was separated by filtration to give 6-(1H-tetrazol-5-yl)thieno[3,2-b]pyridin-5-one (containing $\frac{2}{3}$ mole of water) as a white fibrous solid melting at greater than 300° C.

EXAMPLE 8

If the procedure of Example 7 is repeated using the appropriate oxothienopyridines obtained in the second paragraph of Example 6, the following compounds are obtained:

2-Methyl-6-(1H-tetrazol-5-yl)thieno[2,3-b]pyridin-6(7H)-one.

2,7-Dimethyl-5-(1H-tetrazol-5-yl)thieno[3,4-b]pyridin-4(3H)-one.

What is claimed is:

1. A compound of the formula

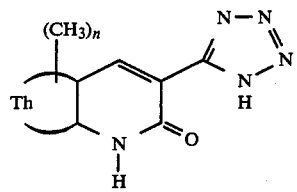

wherein Th is a thiophene fused to the pyridine ring and n is 0, 1 or 2; and the pharmaceutically acceptable salts thereof.

2. A compound according to claim 1 which is 6-(1H-tetrazol-5-yl)thieno[3,2-b]pyridin-5(4H)-one; and the pharmaceutically acceptable salts thereof.

3. A compound according to claim 1 which is 6-(1H-tetrazol-5-yl)thieno[3,2-b]pyridin-5(4H)-one.

* * * * *